United States Patent
Duncan et al.

(12) 
(10) Patent No.: US 9,750,838 B2
(45) Date of Patent: Sep. 5, 2017

(54) WOUND MANAGEMENT SYSTEM AND METHODS OF USING

(71) Applicant: Medline Industries, Inc., Mundelein, IL (US)

(72) Inventors: Angie Duncan, Mundelein, IL (US); Bridget Donovan, Mundelein, IL (US); Debashish Chakravarthy, Mundelein, IL (US); Maria Miller, Mundelein, IL (US)

(73) Assignee: Medline Industries, Inc., Mundelein, IL (US)

( * ) Notice: Subject to any disclaimer, the term of this patent is extended or adjusted under 35 U.S.C. 154(b) by 0 days.

(21) Appl. No.: 14/664,264

(22) Filed: Mar. 20, 2015

(65) Prior Publication Data

US 2015/0265741 A1  Sep. 24, 2015

Related U.S. Application Data

(60) Provisional application No. 61/968,796, filed on Mar. 21, 2014.

(51) Int. Cl.
| | |
|---|---|
| *A61L 15/42* | (2006.01) |
| *A61L 26/00* | (2006.01) |
| *A61L 15/44* | (2006.01) |
| *A61L 15/58* | (2006.01) |

(52) U.S. Cl.
CPC .............. *A61L 15/42* (2013.01); *A61L 15/44* (2013.01); *A61L 15/58* (2013.01); *A61L 26/0061* (2013.01); *A61L 26/0066* (2013.01); *A61L 2300/22* (2013.01); *A61L 2300/404* (2013.01); *A61L 2300/406* (2013.01); *A61L 2300/428* (2013.01)

(58) Field of Classification Search
CPC ......... A61L 2300/404; A61L 2300/406; A61L 2300/412; A61L 2300/428; A61L 2300/61; A61L 24/046
See application file for complete search history.

(56) References Cited

U.S. PATENT DOCUMENTS

| | | | | |
|---|---|---|---|---|
| 5,702,715 A | * | 12/1997 | Nikolaychik | A61L 24/0073 106/124.5 |
| 6,695,515 B1 | * | 2/2004 | Fleury | A61F 17/00 401/132 |
| 7,066,934 B2 | * | 6/2006 | Kirsch | A61B 17/085 602/52 |
| 2003/0153860 A1 | | 8/2003 | Nielsen et al. | |
| 2004/0127835 A1 | | 7/2004 | Sigurjonsson et al. | |
| 2004/0133143 A1 | | 7/2004 | Burton et al. | |
| 2008/0154168 A1 | * | 6/2008 | Lutri | A61F 13/02 602/54 |
| 2010/0159192 A1 | * | 6/2010 | Cotton | A61F 13/02 428/137 |
| 2010/0204667 A1 | | 8/2010 | Chakravarthy | |
| 2013/0012858 A1 | * | 1/2013 | Jackson | A61F 13/02 602/47 |
| 2013/0018336 A1 | | 1/2013 | Pernot | |
| 2013/0237895 A1 | | 9/2013 | Rastegar et al. | |
| 2013/0303654 A1 | * | 11/2013 | Salamone | A61K 31/785 523/111 |

FOREIGN PATENT DOCUMENTS

| | | | | |
|---|---|---|---|---|
| EP | 0353972 | | 1/1994 | |
| WO | WO 2013/076450 A1 | * | 5/2013 | ............. A61L 24/04 |
| WO | WO 2015/143341 | | 9/2015 | |

OTHER PUBLICATIONS

Office Action for U.S. Appl. No. 12/652,964, mailed Feb. 16, 2012, 23 pages.
Office Action for U.S. Appl. No. 12/652,964, mailed Jul. 7, 2016, 28 pages.
Office Action for U.S. Appl. No. 12/652,964, mailed Jan. 22, 2015, 23 pages.
Office Action for U.S. Appl. No. 12/652,964, mailed Aug. 30, 2012, 25 pages.
Office Action for U.S. Appl. No. 12/652,964, mailed Sep. 10, 2015, 23 pages.
International Search Report and Written Opinion for International Application No. PCT/US2015/021782, mailed Jun. 18, 2015, 11 pages.

* cited by examiner

*Primary Examiner* — Aradhana Sasan
(74) *Attorney, Agent, or Firm* — Cooley LLP

(57) ABSTRACT

A wound management system can comprise a surgically acceptable adhesive disposed over a wound and a surgically acceptable film repositionably disposed over the surgically acceptable adhesive, and methods of managing a wound involving the same.

38 Claims, No Drawings

WOUND MANAGEMENT SYSTEM AND METHODS OF USING

CROSS-REFERENCE TO RELATED APPLICATIONS

This application claims priority benefit of U.S. Provisional Application Ser. No. 61/968,796, filed Mar. 21, 2014, the disclosure of which is incorporated by reference herein in its entirety.

BACKGROUND

Wound management systems are used to assist in closing and covering wounds, lacerations, and incisions, for example those caused by surgery. Conventional wound dressings and bandages can be effective in covering and protecting wounds, may not be effective in sealing and aligning the tissue of the wound or incision. Topical skin adhesives (e.g., cyanoacrylates) have been employed to seal and align tissue edges in incisions, but may not be sufficient or effective in covering and protecting the incision. Wound management systems have been proposed where a conventional skin adhesive composition is "reinforced" by applying it over conventional wound dressing materials, such as adhesive tape (e.g., as described in US 2009/0036921), whereby the skin adhesive penetrates the structure of the tape. The resulting "composite" structure reinforces the skin adhesive and may provide a barrier to moisture and contamination. However, such "composite" systems are relatively rigid and tend to be uncomfortable for the patient while the system is in place, and may cause additional trauma or discomfort when it is removed. Further, because such composite wound management systems adhere strongly to the skin, it is not possible to reposition such composites during application, or as needed during the wound healing process. Thus, if a "composite" wound management system is misaligned during application, or becomes misaligned during use, it may be necessary for it to be removed entirely and reapplied, thereby causing additional trauma to the wound. Thus, there is a need for a wound management system that addresses these and other problems.

SUMMARY OF THE INVENTION

A wound management system can comprise a surgically acceptable skin adhesive disposed over a wound and a surgically acceptable film repositionably disposed over the surgically acceptable skin adhesive. The surgically acceptable adhesive can comprise a cyanoacrylate adhesive, such as at least one of butylcyanoacrylate and octylcyanoacrylate, and particularly octylcyanoacrylate.

The surgically acceptable film can be in contact with the surgically acceptable skin adhesive, and can comprise a first side and a second side, the first side having a pressure sensitive adhesive disposed thereon.

The surgically acceptable film can comprise a silicone sheet. In some embodiments, the surgically acceptable film can comprise a silicone adhesive. In other embodiments, the surgically acceptable adhesive can be an atraumatic adhesive.

In some embodiments, the surgically acceptable film can be formed by disposing a curable gel or curable liquid over the surgically acceptable adhesive and curing the curable gel or curable liquid into a surgically acceptable film. In other embodiments, the surgically acceptable film can be permeable to at least one of air, moisture, blood, and wound exudates. In still other embodiments, the surgically acceptable film can be impermeable to at least one of air, moisture, blood, and wound exudates. In yet other embodiments, the surgically acceptable film can be semi-permeable to at least one of air, moisture, blood, and wound exudates.

In particular embodiments, the surgically acceptable film can be transparent or translucent. In other particular embodiments, the surgically acceptable film can be opaque. In yet other embodiments, the surgically acceptable film can be adapted to change from transparent or translucent to opaque.

In some embodiments, the surgically acceptable film can comprise one or more of silicone, paper, cellulose, microporous material, polyamide, polyacrylate, polyester, copolyester, and fabric. In particular embodiments, the surgically acceptable film comprises silicone. For example the surgically acceptable film can have a first surface comprising silicone and a second surface comprising other suitable materials. In still other embodiments, the surgically acceptable film is composed primarily of silicone.

In some embodiments, the surgically acceptable film is perforated, and in other embodiments it is not perforated. In other embodiments, the surgically acceptable film is formed in a pre-determined shape, for example a shape that is suitable for disposition over particular anatomical features, or suitable for disposition over particular types of wounds or incisions. In still other embodiments, the surgically acceptable film is marked with one or more markings delineating one or more pre-determined shapes for the film, whereby a physician can more readily trim the film to a desired shape.

In particular embodiments, the wound management system can further comprise an absorbent dressing disposed over the surgically acceptable film. In other particular embodiments, the wound management system can further comprise at least one topically administrable active agent, for example, one or more of antibiotics, anti-virals, antimicrobials, moisturizers, vitamins, skin nutrients, beneficial oils, and scar reducing agents. In still other embodiments, the wound management system can further comprise both absorbent dressing disposed over the surgically acceptable film, and at least one of the topically administrable active agents described herein.

A method of managing a wound can comprise applying a surgically acceptable skin adhesive to a wound and applying a repositionable surgically acceptable film over the surgically acceptable skin adhesive. In some embodiments, the method can further comprise curing the surgically acceptable skin adhesive, wherein the cured skin adhesive does not impede the repositionability of the surgically acceptable film. In other embodiments of the method, the surgically acceptable skin adhesive can comprise one or more of butylcyanoacrylate and octylcyanoacrylate, and in particular can comprise octylcyanoacrylate.

In particular embodiments, the method can comprise contacting the repositionable surgically acceptable film with the surgically acceptable skin adhesive. In other particular embodiments, the repositionable surgically acceptable film is applied before the surgically acceptable skin adhesive is completely cured. In yet other particular embodiments, the repositionable surgically acceptable film is applied after the surgically acceptable skin adhesive is completely cured.

In some cases, the repositionable surgically acceptable film is a surgically acceptable tape, dressing, or bandage. In particular cases, the repositionable surgically acceptable film is applied as a transparent or translucent film, and becomes opaque over time. In other cases, the method further comprises applying an absorbent dressing over the repositionable surgically acceptable film. In some embodiments, the method further comprises applying a topically acceptable active agent, for example, one or more of antibiotics, anti-virals, anti-microbials, moisturizers, vitamins, skin nutrients, beneficial oils, and scar reducing agents, over the wound.

In some embodiments, the surgically acceptable skin adhesive is applied from a sponge-tipped applicator, a high-density foam applicator, a flocked-tipped applicator, or a silicone-tipped applicator. In particular embodiments, the applicator is a blister-sealed applicator.

The method can further comprise repositioning the repositionable surgically acceptable film after applying the repositionable surgically acceptable film.

DETAILED DESCRIPTION

It should be understood that all publications, journal articles, patents, and the like that are mentioned in this specification are hereby incorporated by reference in their entirety and for all purposes.

Unless otherwise defined, all terms used in this specification are intended to have the meaning that a person of ordinary skill in the art would have ascribed to them at the time of the invention. Certain terms have particular meanings, as follows.

"Repositionable" and conjugations thereof refers to a relationship whereby a plurality elements are connected in such a way that at least one element can be moved in space with respect to at least one other element. With respect to the repositionable surgically acceptable film, the term "repositionable" refers to the ability to remove the surgically acceptable film, either partially or completely from the wound site and replace it in a different position or orientation without appreciably removing or damaging the surgically acceptable skin adhesive, or causing more than a de minimus amount of additional trauma to the wound site. In some embodiments, "repositionable" can refer to the ability of e.g. a physician to completely remove the surgically acceptable film from the wound site, without appreciably removing or damaging the surgically acceptable skin adhesive, or causing more than de minimus amount of additional trauma to wound site, and completely replacing the originally applied surgically acceptable film with another repositionable surgically acceptable film.

"Opaque" refers to substances that have at least 70% opacity. The percent opacity for plastic or polymeric materials can be determined by the ASTM D1746 Standard Test Method for Transparency of Plastic Sheeting, and the opacity of paper materials can be determined by the ASTM D589-97(2007) Standard Test Method for Opacity of Paper.

A material is considered "permeable" if the moisture vapor transmission is at least 301 g/m$^2$, for example about 301-800 g/m$^2$ when tested according to the ASTM E96 Standard Test Method for Water Vapor Transmission of Materials.

A material is considered "semi-permeable" if the moisture vapor transmission is about 101-300 g/m$^2$ when tested according to the ASTM E96 Standard Test Method for Water Vapor Transmission of Materials.

A material is considered "impermeable" if the moisture vapor transmission is less than about 100 g/m$^2$ when tested according to the ASTM E96 Standard Test Method for Water Vapor Transmission of Materials.

"Butylcyanoacrylate" is sometimes known in the art as "butyl cyanoacrylate" and can include any of n-butylcyanoacrylate, iso-butylcyanoacrylate, sec-butylcyanoacrylate, and tert-butylcyanoacrylate, either alone or in any combination, and particularly n-butylcyanoacrylate.

"Octylcyanoacrylate" is sometimes known in the art as "octyl cyanoacrylate" and can include any isomer thereof alone or multiple isomers in any combination, and particularly straight-chained octylcyanoacrylate.

One of skill in the art understands that other cyanoacrylates can be substituted for butylcyanoacrylate or octylcyanoacrylate provided that such other cyanoacrylates provide acceptable skin adhesive properties similar to those of butylcyanoacrylate or octylcyanoacrylate.

The wound management systems of the present invention can comprise a surgically acceptable skin adhesive disposed over a wound and a surgically acceptable film repositionably disposed over the surgically acceptable skin adhesive. Repositionable films can be in any form such as gauzes, bandages, tape, sheets, and the like, so long as the film can be repositioned after its initial application. The repositionable disposition of the film can have a variety of advantages over films that are not repositionable. For example, because a repositionably disposed film is not strongly adhered to the skin adhesive, the resulting wound management system is more flexible (less rigid) than a wound management system in which the film and skin adhesive form an integrated composite (e.g., systems in which the adhesive penetrates the film, thereby incorporating the film within the adhesive). This increased flexibility substantially increases patient comfort and reduces trauma upon removal of the wound management system after wound healing is complete. Also, because the surgically acceptable film component of wound management systems of the present invention are repositionable, if the film is not initially applied in the ideal location, as can happen in emergency or high stress situations, then the film can be repositioned to a more ideal location at a later time. Similarly, if the ideal position of a repositionable film changes during the course of wound healing, for example, because of changes in the wound, it can be repositioned as needed.

The surgically acceptable skin adhesive can comprise any suitable skin adhesive, particularly a cyanoacrylate adhesive. Any cyanoacrylate suitable for use as a skin adhesive can be used. In particular, the cyanoacrylate skin adhesive can comprise at least one of butylcyanoacrylate and octylcyanoacrylate, and more particularly can comprise octylcyanoacrylate. The surgically acceptable skin adhesive, such as any of the surgically acceptable skin adhesives described herein, can be an atraumatic adhesive, for example, a silicone adhesive. Examples of suitable surgically acceptable skin adhesives include SurgiSeal® and Skinaffix® (both available from Medline).

The surgically acceptable film can be disposed over the surgically acceptable skin adhesive. Thus, the surgically acceptable film can contact the surgically acceptable skin adhesive, although this is not required unless otherwise specified.

The surgically acceptable film can be any film that can be used in surgery, and can have any surgically acceptable shape, size, or content, depending on the intended use, size and type of wound to be managed, and other factors understood in the art.

The surgically acceptable film can comprise one or more of silicone, paper, cellulose, microporous material, polyamide, polyurethane, polyacrylate, polyester, copolyester, and fabric. In particular, the surgically acceptable films can comprise silicone, although no particular components are required unless otherwise specified. Examples of suitable surgically acceptable films include Gentac® (available from Medline).

The surgically acceptable film can be in any suitable form. For example, the surgically acceptable film can be in the form of a sheet, dressing, or tape, although this is not required unless otherwise specified. In particular, the surgically acceptable film can be in the form of a silicone sheet. Depending on the intended use, the surgically acceptable film can be either perforated or not perforated.

The surgically acceptable film can further comprise a film adhesive, such as a silicone adhesive or a pressure sensitive adhesive. When the surgically acceptable film has a first side and a second side, a pressure sensitive film adhesive can be disposed on the first side. The film adhesive can be an atraumatic adhesive. The atraumatic film adhesive can be one that does not strongly adhere to the surgically acceptable skin adhesive or to the patient's skin, but instead allows the surgically acceptable film to be repositioned. Such film adhesives can be low-tack, reusable, pressure sensitive adhesives, for example, sphere shaped acrylic adhesives such as those used in conjunction with repositionable articles such as POST-IT® notes. In addition, many silicone adhesives are repositionable.

The surgically acceptable film can be formed before being disposed on the surgically acceptable adhesive (e.g., provided as a pre-formed sheet or tape), or can be formed in situ over the surgically acceptable skin adhesive. In the latter case, the surgically acceptable film can be formed by disposing a curable gel or curable liquid over the surgically acceptable skin adhesive and curing the curable gel or curable liquid into a surgically acceptable film.

The surgically acceptable film can be permeable to at least one of air, moisture, blood, and wound exudates. Such film can be useful in situations where it is beneficial to allow passage of at least one of air, moisture, blood, and wound exudates through the film. For example, when wound healing would be benefitted by allowing wound exudates, such as puss, to drain from the wound site, a permeable film can be desirable. Permeable films can include, for example, permeable gauze or paper, although some gauze and paper can be semi-permeable or impermeable.

The surgically acceptable film can be semi-permeable to at least one of air, moisture, blood, and wound exudates. Such films can be useful in situations where it is beneficial to allow limited passage of at least one of air, moisture, blood, and wound exudate through the film. Semi-permeable films can include, for example, semi-permeable polyamides or polyurethanes, although some polyamide and polyurethane films can be permeable or impermeable.

The surgically acceptable film can be impermeable to at least one of air, moisture, blood, and wound exudates. Such films can be useful in situations where it is beneficial to minimize or prevent the passage of at least one of air, moisture, blood, and wound exudates through the film. For example, when a wound at risk for infection, an impermeable film may reduce the risk of infection. Impermeable films can include, for example, silicone or polyurethane, although some silicone and polyurethane films can be permeable or semi-permeable.

The surgically acceptable film can be transparent or translucent. In such cases, it can be possible to observe the wound through the surgically acceptable film without removing the surgically acceptable film. Transparent and translucent films can be made out of any transparent or translucent material, such as transparent or translucent silicone, polyurethane, and the like.

The surgically acceptable film can be opaque, in which case the wound can be concealed, for example, for cosmetic purposes. Opaque films can be made by adding a surgically acceptable dye to an otherwise transparent or translucent material, or by using a material that is opaque (e.g., opacifying agents such as inorganic fillers such as titanium dioxide) without the addition of a dye.

The surgically acceptable film can be transparent or translucent when first applied, and then become opaque over time. The color change can occur, for example, by oxidation of the surgically acceptable film or by reaction of one or more components of the surgically acceptable film with wound exudate.

The surgically acceptable film can be provided in a pre-determined shape, such as a rectangle, square, circle, and the like, or irregularly configured to better conform to the contours of a patient's anatomy. In addition or in the alternative, the surgically acceptable film can be provided with one or more markings delineating one or more pre-determined shapes on the film. The one or more markings can be a guide, allowing the user to easily cut the surgically acceptable film into one or more of the pre-determined shapes, depending on the intended use, the size of the wound, the type of the wound, etc. The surgically acceptable film can also be provided partially (e.g., "Kiss Cut") or completely precut, optionally on a release film or liner.

The wound management system can further comprise an absorbent dressing disposed over the surgically acceptable film. The absorbent dressing can be any absorbent dressing known in the art, and can comprise, for example, one or more of textiles, wovens, non-wovens, fabrics, bandages, gauze, and the like.

The wound management system can further comprise at least one active agent, for example to aid in wound healing. Exemplary active agents include one or more of antibiotics, anti-virals, antimicrobials, moisturizers, vitamins, skin nutrients, beneficial oils, and scar reducing agents. The active agent can be incorporated into one or more of the surgically acceptable skin adhesive, the surgically acceptable film, or a separate active agent containing layer.

In use, a method of managing a wound can comprise applying the wound management system described herein to a wound. For example, a method of managing a wound can comprise applying a surgically acceptable skin adhesive, such as any of the surgically acceptable skin adhesives described herein, to a wound, and applying a repositionable surgically acceptable film, such as any of the surgically acceptable films described herein, over the surgically acceptable skin adhesive. The method can further comprise repositioning the repositionable surgically acceptable film after it is applied.

In many cases, it is advantageous to limit or prevent the surgically acceptable skin adhesive from entering the wound, although this is not required unless otherwise specified. This can be accomplished, for example, by drawing skin or other uninjured tissue around the wound together before applying the surgically acceptable skin adhesive, by applying a surgically acceptable skin adhesive that cures rapidly upon application so that it does not have time to enter the wound, or by providing a surgically acceptable skin adhesive with sufficiently high viscosity so as to reduce or eliminate flow of the skin adhesive into the wound.

The surgically acceptable skin adhesive can be applied over the wound by any method known in the art. Typically, the surgically acceptable skin adhesive will be applied to the wound as a curable liquid or gel. In such cases, the curable liquid or gel can be applied by pouring or dropping, such as with a medicine dropper, the curable liquid or gel over the wound. Alternatively, such curable liquids or gels can be applied with an applicator. Suitable applicators include one or more of a sponge-tipped applicator, a high-density foam applicator, a flocked-tipped applicator, and a silicone-tipped applicator. The applicator can be blister-sealed.

When the surgically acceptable skin adhesive is applied as a liquid or gel that is cured over the wound, the repositionable surgically acceptable film can be applied either before or after the surgically acceptable skin adhesive is cured. For example, if the repositionable surgically acceptable film is applied after the surgically acceptable skin adhesive is cured, it can be adapted (e.g., by appropriate selection of film material and/or film adhesive) to provide a relatively weak, repositionable or removable bond to the cured surgically acceptable skin adhesive such that later repositioning of the film is possible. Similarly, if the surgically acceptable film is applied before the surgically acceptable skin adhesive is cured, the surface of the film (or film adhesive) contacting the uncured skin adhesive should form a relatively weak, repositionable bond to the skin adhesive, once it cures. As yet another example, the repositionable surgically acceptable film can comprise a silicone sheet, or a sheet with a silicone surface, that "wets" the surgically acceptable skin adhesive or the subject in a manner similar to that of a surfactant, thereby repositionably and reversibly attaching to one or both of the surgically acceptable skin adhesive and the skin. In such embodiments, a film adhesive may not be required to provide a repositionable bond between the repositionable film and the skin adhesive. Variations of and alternatives to these exemplary strategies for preventing integration of the surgically acceptable skin adhesive and the surgically acceptable film will be apparent to a person of ordinary skill in the art.

The step of applying the surgically acceptable film can comprise contacting the surgically acceptable skin adhesive with the surgically acceptable film. Alternatively, another material, such as a wound-healing layer, an absorbent layer, and the like, can be placed between the surgically acceptable skin adhesive and the surgically acceptable film.

The method can further comprise applying an absorbent dressing, such as those discussed herein or others known in the art, over the surgically acceptable film.

The method can further comprise applying a pharmaceutically acceptable active agent to the wound. The active agent can be, for example, one or more of antibiotics, anti-virals, antimicrobials, moisturizers, vitamins, skin nutrients, beneficial oils, and scar reducing agents. The wound management system of the present invention can be removed in 5-7 days after surgery, or after complete healing (typically about 14 days), but can vary depending on the nature of the wound and the patient.

The wound management system disclosed herein can also be provided in the form of a kit. The kit can contain an uncured surgically acceptable skin adhesive in the form of a liquid or gel, and one or more surgically acceptable films. Alternatively, the kit can include an uncured surgically acceptable skin adhesive, and a curable liquid or gel that can be cured to form a surgically acceptable film. The surgically acceptable skin adhesive and film can be one of those described herein, or any other film or skin adhesive that is acceptable for use in surgery. The amount of surgically acceptable skin adhesive and surgically acceptable film in the kit can vary depending on the size of wound the kit is configured to treat. For example, a kit for treating small or minor wounds can be provided with relatively small amounts of the surgically acceptable skin adhesive and film, whereas kits for treating major or serious wounds or surgery can be provided with larger amounts of the surgically acceptable skin adhesive and film. For example, the amount of skin adhesive can be about 0.1 to 10 mL, including about 0.1, 0.5, 1, 2, 3, 4, 5, 6, 7, 8, 9, or 10 mL, inclusive of all ranges and subranges therebetween. The amount of surgically acceptable film can include particular non-limiting embodiments that are described in the following examples.

EXAMPLE 1

A subject has a laceration approximately 5 inches long on the abdomen. The skin on the sides of the laceration is pulled together, and an octylcyanoacrylate skin adhesive is applied over the wound using a blister sealed silicone tipped applicator. The adhesive is cured to seal the wound. A surgically acceptable skin film, in the form of a 4 inch by 6 inch rectangular dressing containing a topical antimicrobial ointment and low-tack pressure sensitive adhesive, is placed over the octylcyanoacrylate adhesive. The dressing is repositioned as necessary to optimally cover the wound. After the wound is healed, the dressing is removed without disturbing the scar or causing excessive pain to the subject.

EXAMPLE 2

A subject has an avulsion on the torso with an unevenly shaped skin flap. The skin flap is pulled over the avulsion, and a mixture of octylcyanoacrylate and butylcyanoacrylate is applied over the skin flap to seal the wound. A curable silicone gel is applied over the cyanoacrylate adhesive and allowed to cure to form a repositionable film. The adhesive and film are transparent, allowing the user to monitor the course of wound healing by visual inspection.

EXAMPLE 3

A patient had multiple wounds. One wound was treated by applying a surgical mesh having a curing accelerator (for accelerating the curing of cyanoacrylates) over the wound. An octylcyanoacrylate skin adhesive was applied over the mesh. The resultant glue/mesh composite formed well-supported wound seal, but was intensely uncomfortable for the patient. The patient requested that the composite be removed, however, such removal was not possible because the composite was strongly adhered to the patient's skin such that tearing it off would reopen the wound.

EXAMPLE 4

A second wound on the same patient described in Example 3 was sealed with an octylcyanoacrylate skin adhesive, which was allowed to cure. A repositionable nonwoven film containing an antimicrobial and silicon skin adhesive (sold under the name Optifoam® Gentile Antimicrobial Post-Op Strip) was affixed over the cured octylcyanoacrylate adhesive. The patient reported a high level of comfort with this system, which did not overly restrict patient movement.

The various embodiments described herein allow a person of ordinary skill in the art to make, use, and practice the invention. However, such embodiments are not intended to be limiting, unless otherwise specified. For example, while various specific surgically acceptable adhesives and films have been described for illustrative purposes, such specific elements are not intended to be limiting. Indeed, a person of ordinary skill in the art will find variations, substitutions, and changes that are within the spirit and scope of the invention.

We claim:

1. A wound management system, comprising
a surgically acceptable cyanoacrylate skin adhesive disposed over and in direct contact with a wound; and
a surgically acceptable film disposed over the surgically acceptable skin adhesive, wherein the surgically acceptable film is in contact with and repositionably binds to a cured surgically acceptable skin adhesive when the surgically acceptable skin adhesive is in direct contact with the wound, and wherein both the surgically acceptable cyanoacrylate skin adhesive and the surgically acceptable film cover the wound.

2. The wound management system of claim 1, wherein the surgically acceptable skin adhesive comprises at least one of butylcyanoacrylate and octylcyanoacrylate.

3. The wound management system of claim 2, wherein the surgically acceptable adhesive comprises octylcyanoacrylate.

4. The wound management system of claim 1, wherein the surgically acceptable film comprises a first side and a second side, the first side having a pressure sensitive adhesive disposed thereon.

5. The wound management system of claim 1, wherein the surgically acceptable film comprises a silicone sheet.

6. The wound management system of claim 1, wherein the surgically acceptable film comprises a silicone adhesive.

7. The wound management system of claim 1, wherein the surgically acceptable film is formed by disposing a curable gel or curable liquid over the surgically acceptable skin adhesive and curing the curable gel or curable liquid into a film.

8. The wound management system of claim 1, wherein the surgically acceptable film is permeable to at least one of air, moisture, blood, and wound exudate.

9. The wound management system of claim 1, wherein the surgically acceptable film is semi-permeable to at least one of air, moisture, blood, and wound exudate.

10. The wound management system of claim 1, wherein the surgically acceptable film is impermeable to at least one of air, moisture, blood, and wound exudate.

11. The wound management system of claim 1, wherein the surgically acceptable film is transparent or translucent.

12. The wound management system of claim 1, wherein the surgically acceptable film is opaque.

13. The wound management system of claim 1, wherein the surgically acceptable film is adapted to change from transparent or translucent to opaque.

14. The wound management system of claim 1, wherein the surgically acceptable film is in the form of a surgically acceptable tape, dressing or bandage.

15. The wound management system of claim 1, wherein the surgically acceptable adhesive is an atraumatic adhesive.

16. The wound management system of claim 1, wherein the surgically acceptable film comprises one or more of silicone, paper, cellulose, microporous material, polyamide, polyacrylate, polyester, copolyester, and fabric.

17. The wound management system of claim 16, wherein the surgically acceptable film comprises silicone.

18. The wound management system of claim 17, wherein the surgically acceptable film has a first surface comprising silicone and a second surface comprising one or more of paper, cellulose, microporous material, polyamide, polyacrylate, polyester, copolyester, and fabric.

19. The wound management system of claim 1, wherein the surgically acceptable film is perforated.

20. The wound management system of claim 1, wherein the surgically acceptable film is not perforated.

21. The wound management system of claim 1, further comprising an absorbent dressing disposed over the surgically acceptable film.

22. The wound management system of claim 1, further comprising at least one topically administrable active agent.

23. The wound management system of claim 22, wherein the topically administrable active agent comprises one or more of antimicrobials, moisturizers, vitamins, skin nutrients, beneficial oils, and scar reducing agents.

24. The wound management system of claim 1, wherein the surgically acceptable film comprises one or more markings delineating one or more pre-determined shapes on the film.

25. A method of managing a wound, comprising
applying a surgically acceptable cyanoacrylate skin adhesive directly to a wound; and
then applying a repositionable surgically acceptable film over the surgically acceptable skin adhesive wherein the surgically acceptable film is contacted with and bonds to the surgically acceptable skin adhesive, and wherein both the surgically acceptable cyanoacrylate skin adhesive and the surgically acceptable film cover the wound.

26. The method of claim 25, further comprising curing the surgically acceptable skin adhesive, wherein the cured skin adhesive does not impede the repositionability of the surgically acceptable film.

27. The method of claim 25, wherein the surgically acceptable skin adhesive comprises one or more of butylcyanoacrylate and octylcyanoacrylate.

28. The method of claim 25, wherein the surgically acceptable skin adhesive comprises octylcyanoacrylate.

29. The method of claim 25, wherein the repositionable surgically acceptable film is applied before the surgically acceptable skin adhesive is completely cured.

30. The method of claim 25, wherein the repositionable surgically acceptable film is applied after the surgically acceptable skin adhesive is completely cured.

31. The method of claim 25, wherein the repositionable surgically acceptable film is a surgically acceptable tape, dressing, or bandage.

32. The method of claim 25, wherein the surgically acceptable film is applied as a transparent or translucent film, and becomes opaque over time.

33. The method of claim 25, further comprising applying an absorbent dressing over the repositionable surgically acceptable film.

34. The method of claim 25, further comprising applying a topically acceptable active agent to the wound.

35. The method of claim 34, wherein the topically acceptable active agent includes one or more of anti-microbials, moisturizers, vitamins, skin nutrients, beneficial oils, and scar reducing agents.

36. The method of claim 25, wherein the surgically acceptable skin adhesive is applied from a sponge-tipped applicator, a high-density foam applicator, a flocked-tipped applicator, or a silicone-tipped applicator.

37. The method of claim 36, wherein the applicator is a blister-sealed applicator.

38. The method of claim 25, further comprising repositioning the repositionable surgically acceptable film after applying the repositionable surgically acceptable film.

* * * * *